United States Patent [19]
Mapes

[11] Patent Number: 5,874,216
[45] Date of Patent: Feb. 23, 1999

[54] INDIRECT LABEL ASSAY DEVICE FOR DETECTING SMALL MOLECULES AND METHOD OF USE THEREOF

[75] Inventor: James P. Mapes, Raleigh, N.C.

[73] Assignee: EnSys Environmental Products, Inc., Durham, N.C.

[21] Appl. No.: 606,385

[22] Filed: Feb. 23, 1996

[51] Int. Cl.⁶ .................................................. G01N 33/533
[52] U.S. Cl. .................... 435/6; 422/56; 422/57; 422/58; 422/59; 422/60; 435/7.1; 435/7.2; 435/7.92; 435/7.95; 435/287.7; 435/287.9; 435/962; 435/969; 435/970; 436/518; 436/524; 436/530; 436/538; 436/541; 436/823; 436/825
[58] Field of Search ................ 422/56–60; 435/7.1–7.2, 435/7.92–7.95, 287.7, 287.8, 287.9, 962, 969, 970; 436/518, 524, 530, 538, 541, 823, 825

[56] References Cited

U.S. PATENT DOCUMENTS

| | | |
|---|---|---|
| 3,904,367 | 9/1975 | Golibersuch . |
| 3,951,748 | 4/1976 | Devlin . |
| 4,153,675 | 5/1979 | Kleinerman . |
| 4,166,844 | 9/1979 | Tu . |
| 4,168,146 | 9/1979 | Grubb et al. . |
| 4,467,554 | 8/1984 | Russell . |
| 4,650,751 | 3/1987 | Seigel et al. . |
| 4,657,739 | 4/1987 | Yasuda et al. . |
| 4,661,444 | 4/1987 | Li . |
| 4,666,863 | 5/1987 | Edwards et al. . |
| 4,670,381 | 6/1987 | Frickey et al. . |
| 4,703,017 | 10/1987 | Campbell et al. . |
| 4,714,672 | 12/1987 | Rokugawa et al. . |
| 4,716,123 | 12/1987 | Wood . |
| 4,769,333 | 9/1988 | Dole et al. . |
| 4,772,550 | 9/1988 | Greenquist . |
| 4,786,589 | 11/1988 | Rounds . |
| 4,806,311 | 2/1989 | Greenquist . |
| 4,837,145 | 6/1989 | Liotta . |
| 4,857,453 | 8/1989 | Ullman et al. . |
| 4,859,603 | 8/1989 | Dole et al. . |
| 4,859,612 | 8/1989 | Cole et al. . |
| 4,861,552 | 8/1989 | Masuda et al. . |
| 4,868,106 | 9/1989 | Ito et al. . |
| 4,868,108 | 9/1989 | Bahar et al. . |
| 4,874,710 | 10/1989 | Piran . |
| 4,879,215 | 11/1989 | Weng et al. . |
| 4,882,288 | 11/1989 | North et al. . |
| 4,904,583 | 2/1990 | Mapes et al. . |
| 4,943,522 | 7/1990 | Eisinger et al. . |
| 4,943,525 | 7/1990 | Dawson . |
| 4,956,302 | 9/1990 | Gordon et al. . |
| 4,962,021 | 10/1990 | Meserol et al. . |
| 4,962,022 | 10/1990 | Fleming et al. . |
| 4,978,502 | 12/1990 | Dole et al. . |
| 4,983,529 | 1/1991 | Stewart et al. . |
| 5,028,535 | 7/1991 | Buschler et al. . |
| 5,030,558 | 7/1991 | Litman et al. . |
| 5,057,412 | 10/1991 | Rabin et al. . |
| 5,073,484 | 12/1991 | Swanson et al. . |
| 5,075,078 | 12/1991 | Osikowicz et al. . |
| 5,085,987 | 2/1992 | Olson . |
| 5,085,988 | 2/1992 | Olson . |
| 5,089,391 | 2/1992 | Buechler et al. . |
| 5,120,662 | 6/1992 | Chan et al. . |
| 5,139,934 | 8/1992 | Stewart et al. . |

(List continued on next page.)

FOREIGN PATENT DOCUMENTS

| | | |
|---|---|---|
| 0 421 294 | 4/1991 | European Pat. Off. . |
| 0 296 724 B1 | 1/1995 | European Pat. Off. . |
| 88/08534 | 11/1988 | WIPO . |
| WO 93/17338 | 9/1993 | WIPO . |

*Primary Examiner*—Christopher L. Chin
*Assistant Examiner*—Bao-Thuy L. Nguyen
*Attorney, Agent, or Firm*—Jones & Askew, LLP

[57] ABSTRACT

A chromatographic strip positive readout binding assay device and method suitable for quick, sensitive and reliable field testing for small molecules such as environmental contaminants, drugs of abuse, therapeutic drugs and hormones. The detectable label is not attached to either the analyte or to the analyte receptor. Low affinity binding pairs can be used in the positive readout binding assay.

28 Claims, 1 Drawing Sheet

U.S. PATENT DOCUMENTS

| | | |
|---|---|---|
| 5,149,626 | 9/1992 | Fleming . |
| 5,155,022 | 10/1992 | Naqui et al. . |
| 5,156,952 | 10/1992 | Litman et al. . |
| 5,158,869 | 10/1992 | Pouletty et al. . |
| 5,171,695 | 12/1992 | Ekins . |
| 5,188,937 | 2/1993 | Schulte et al. . |
| 5,196,306 | 3/1993 | Bobrow et al. . |
| 5,196,351 | 3/1993 | Harris et al. . |
| 5,198,368 | 3/1993 | Khalil et al. . |
| 5,206,177 | 4/1993 | Delacroix et al. . |
| 5,206,178 | 4/1993 | Monji et al. . |
| 5,210,015 | 5/1993 | Gelfand et al. . |
| 5,212,065 | 5/1993 | Pegg et al. . |
| 5,217,905 | 6/1993 | Marchand et al. . |
| 5,219,730 | 6/1993 | Potocnzak et al. . |
| 5,229,073 | 7/1993 | Luo et al. . |
| 5,232,835 | 8/1993 | Litman et al. . |
| 5,236,826 | 8/1993 | Marshall . |
| 5,242,804 | 9/1993 | Bahar et al. . |
| 5,242,837 | 9/1993 | Slovacek et al. . |
| 5,244,815 | 9/1993 | Guirguis . |
| 5,256,372 | 10/1993 | Brooks et al. . |
| 5,256,532 | 10/1993 | Meinicoff et al. . |
| 5,279,935 | 1/1994 | Nycz . |
| 5,279,943 | 1/1994 | Mathis et al. . |
| 5,306,622 | 4/1994 | Mangold . |
| 5,308,775 | 5/1994 | Donovan et al. . |
| 5,310,687 | 5/1994 | Bard et al. . |
| 5,324,635 | 6/1994 | Kawsec et al. . |
| 5,328,831 | 7/1994 | Stewart et al. . |
| 5,334,537 | 8/1994 | Lee et al. . |
| 5,354,658 | 10/1994 | Wright . |
| 5,360,717 | 11/1994 | Schuy . |
| 5,370,994 | 12/1994 | Stewart et al. . |
| 5,376,556 | 12/1994 | Tarcha et al. . |
| 5,387,503 | 2/1995 | Selmer et al. . |
| 5,395,752 | 3/1995 | Law et al. . |
| 5,395,754 | 3/1995 | Lambotte et al. . |
| 5,399,486 | 3/1995 | Cathey et al. . |
| 5,415,994 | 5/1995 | Imrich et al. . |
| 5,424,193 | 6/1995 | Pronovost et al. . |
| 5,429,929 | 7/1995 | Latov et al. . |
| 5,432,099 | 7/1995 | Ekins . |
| 5,449,611 | 9/1995 | Friedman et al. . |
| 5,451,504 | 9/1995 | Fitzpatrick et al. . |
| 5,459,078 | 10/1995 | Kline et al. . |
| 5,460,940 | 10/1995 | Yves et al. . |
| 5,468,606 | 11/1995 | Bogart et al. . |
| 5,470,702 | 11/1995 | Hovanessian et al. . |
| 5,470,711 | 11/1995 | Bean et al. . |
| 5,482,830 | 1/1996 | Bogart et al. . |
| 5,486,452 | 1/1996 | Gordon et al. . |
| 5,489,510 | 2/1996 | Lopukhin et al. . |
| 5,494,830 | 2/1996 | Hubscher . |

_Fig_1

INDIRECT LABEL ASSAY DEVICE FOR DETECTING SMALL MOLECULES AND METHOD OF USE THEREOF

FIELD OF THE INVENTION

The present invention relates generally to the field of binding assay devices and methods, and more specifically to a binding assay device and method for detecting and quantifying analyte, particularly small molecular weight molecules.

BACKGROUND OF THE INVENTION

The field of immunochemistry, and the development of immunoassay technology, has been evolving since the late 19th century. However, the majority of these methods have been developed for use by the medical community. Immunoassays are based on the highly specific binding between and antibody and the antigen recognized by the antibody. Antibodies are binding proteins that are produced by the immune system of vertebrates in response to substances that are perceived to be foreign.

Various approaches have been described for carrying out immunoassays. The early ELISA's were what is commonly called a "competitive" assay in which the enzyme labeled antigen or antibody competed with the antigen or antibody to be determined for a reaction site on a bead, pad or surface to which one member of an immunologically coupling pair was attached. Subsequently, the "sandwich" assay was developed. In the sandwich assay, the antibody or antigen to be determined was "sandwiched" by an immunochemical reaction between a solid surface treated with an immunological species reactive with the species to be determined and the same or a different reactive immunological species which has been coupled to a signal generating label.

Immunoassay methods combine the specific binding characteristics of an antibody molecule with a read-out system that is used to detect and quantify compounds. Immunochemical assays are reliable when used in the screening of soil for contamination and have been used commercially for the rapid analysis of a variety of compounds, and have been developed to detect a number of different compounds of environmental concern.

In the immunology field the term "hapten" refers to compounds that are unable to directly stimulate antibody production when injected into an animal, but are capable of binding to antibodies if they are produced by an alternate means. Many small molecules do not stimulate the immune system to produce antibodies. Antibodies can be raised, however, that specifically bind to such small molecule haptens. For example, many environmental contaminants, although potentially toxic to humans and animals, do not elicit a strong antibody response.

A "binding assay" is an assay for at least one analyte which may be detected by the formation of a complex between the analyte and an analyte receptor capable of specific interaction with that analyte. The analyte may be haptens, hormones, peptides, proteins, deoxyribonucleic acid (DNA), ribonucleic acids (RNA), metabolites of the aforementioned materials and other substances of either natural or synthetic origin which may be of diagnostic interest and have a specific ligand receptor therefor. Binding assays are generally useful for the in vitro determination of the presence and concentration of analyte in body fluids, food products, animal fluids, and environmental samples. For example, the determination of specific hormones, peptides, proteins, therapeutic drugs, and toxic drugs in human blood or urine has significantly improved the medical diagnosis of the human condition.

Current binding assay technology benefits from the diversity of detection systems developed that use enzyme-catalyzed chromogenic reactions, radionuclides, chemiluminescence, bioluminescence, fluorescence, fluorescence polarization, a variety of potentiometric and optical biosensor techniques and visual labels such as latex beads, gold particles and carbon black.

There is a continuing need for simple, rapid assays for the qualitative, semi-quantitative, and quantitative determination of such analytes in a sample. Furthermore, in many situations, such assays need to be simple enough to be performed and interpreted by non-technical users.

Binding assays rely on the binding of analyte by analyte receptors to determine the concentrations of analyte in a sample. Analyte-receptor assays can be described as either competitive or non-competitive. Non-competitive assays generally utilize analyte receptors in substantial excess over the concentration of analyte to be determined in the assay. Sandwich assays, in which the analyte is detected by binding to two analyte receptors, one analyte receptor labeled to permit detection and a second analyte receptor, frequently bound to a solid phase, to facilitate separation from unbound reagents, such as unbound labeled first analyte receptor, are examples of non-competitive assays.

Competitive assays generally involve a sample suspected of containing analyte, an analyte-analogue conjugate, and the competition of these species for a limited number of binding sites provided by the analyte receptor. Competitive assays can be further described as being either homogeneous or heterogeneous. In homogeneous assays all of the reactants participating in the competition are mixed together and the quantity of analyte is determined by its effect on the extent of binding between analyte receptor and analyte-conjugate or analyte analogue-conjugate. The signal observed is modulated by the extent of this binding and can be related to the amount of analyte in the sample. U.S. Pat. No. 3,817,837 describes such a homogeneous, competitive assay in which the analyte analogue conjugate is a analyte analogue-enzyme conjugate and the analyte receptor, in this case an antibody, is capable of binding to either the analyte or the analyte analogue. The binding of the antibody to the analyte analogue-enzyme conjugate decreases the activity of the enzyme relative to the activity observed when the enzyme is in the unbound state. Due to competition between unbound analyte and analyte analogue-enzyme conjugate for analyte-receptor binding sites, as the analyte concentration increases the amount of unbound analyte analogue-enzyme conjugate increases and thereby increases the observed signal. The product of the enzyme reaction may then be measured kinetically using a spectrophotometer.

Heterogeneous, competitive assays require a separation of analyte analogue conjugate bound to analyte receptor from the free analyte analogue conjugate and measurements of either the bound or the free fractions. Separation of the bound from the free may be accomplished by removal of the analyte receptor and anything bound to it from the free analyte analogue conjugate by immobilization of the analyte receptor on a solid phase or precipitation. The amount of the analyte analogue conjugate in the bound or the free fraction can then be determined and related to the concentration of the analyte in the sample. Normally the bound fraction is in a convenient form, for example, on a solid phase, so that it can be washed, if necessary, to remove remaining unbound analyte analogue conjugate and the measurement of the bound analyte analogue conjugate or related products is facilitated. The free fraction is normally in a liquid form that is generally inconvenient for measurements. If multiple analytes are being determined in a single assay, the determination of the free fraction of analyte analogue conjugate for each analyte is made impossible if all are mixed in a single liquid unless the responses of the individual analyte analogue conjugates can be distinguished in some manner. However, detecting the free fraction of analyte analogue conjugate in assays that are visually interpreted is a distinct advantage because the density of the color developed in such assays is generally proportional to the analyte concentration over much of the range of analyte concentration.

One method that can be used to detect the free analyte analogue conjugate in a heterogeneous, competitive analyte-receptor assay process is to provide a second, immobilized receptor specific for the analyte on a solid phase so that the analyte analogue conjugate not bound to the first analyte receptor can be bound to the second analyte receptor immobilized on the solid phase.

A serious problem with this approach is that the concentration of analyte in the sample may be several orders of magnitude larger than the concentration of analyte analogue conjugate used in the assay process. Under these circumstances, the analyte and the analyte analogue conjugate compete for the available binding sites on the first analyte receptor resulting in essentially all of the analyte analogue conjugate being free in the assay fluid. When the assay fluid is contacted with the immobilized second receptor, the free analyte and the free analyte analogue conjugate compete for binding sites provided by the second analyte receptor. The excess of free analyte is such that its concentration remains several orders of magnitude larger than that of the free analyte analogue conjugate so that the second analyte receptor binding sites on the solid phase are substantially filled by the analyte. The result of this assay process is that little or no signal may be observed on the solid phase when the concentration of the analyte in the sample is high when in fact the assay should be designed to produce the maximum response for such concentrations of analyte.

In European Patent Application No. 87309724.0, a method is described where the sample suspected of containing the analyte and a analyte analogue conjugate are contacted with a bibulous strip that contains immobilized analyte receptor. When sufficient analyte is present in the sample, free analyte analogue conjugate travels beyond the first immobilized analyte receptor zone and contacts a situs where either analyte receptor or another receptor capable of binding the analyte analogue conjugate is immobilized. If the receptor at the situs is receptor for the analyte, then the problem of competition in the presence of high concentrations of analyte exists as described above. Methods are described where the receptor at the situs is a receptor that binds to a species other than the analyte analogue on the free analyte analogue conjugate so that high concentrations of free analyte do not compete for binding sites at the situs. The use of such receptors at the situs requires the development of additional analyte-receptor pairs for analytes unrelated to the analyte for each analyte to be assayed and restricts these assays to formats where the analyte receptor is immobilized on a solid phase. Under these circumstances the assay of multiple analytes in a single assay becomes complex and difficult to develop.

The method described in U.S. Pat. No. 4,506,009 utilizes an analyte analogue conjugate which has both the analyte analogue and an insolubilizing binding component coupled to the signal development element. An insolubilizing receptor is used to precipitate the free analyte analogue conjugate unless it is sterically hindered by the binding of the antibody specific for analyte to the analyte analogue. This method overcomes some of the deficiencies of the prior art because it provides a method to determine the free fraction of analyte analogue conjugate without interference from the free analyte, but it requires the coupling of two elements, the analyte analogue and the insolubilizing binding component, to the signal development element in such a way that the binding of the antibody to the analyte analogue sterically prevents the binding of the insolubilizing receptor to the insolubilizing binding component. The relative and absolute amounts of the analyte analogue and the insolubilizing binding component that are coupled to the signal development element must be empirically selected to achieve the desired result. The need for such manipulation is both time consuming and may limit the assay performance by restricting the ratio of analyte analogue per signal development element.

U.S. Pat. Nos. 4,094,647, 4,235,601 and 4,361,537, describe a test strip for determining a characteristic of a sample comprising a length of material capable of transporting a developing liquid by capillary action and having zones between its ends for receiving the sample and holding reagents. The strip is used for performing binding assays, particularly those in which a radioisotope is used as a label, such as radioimmunoassays. Minute sample sizes may be used. The strip is capable of application to analytical methods having sensitivities below 0.1 mg/ml.

U.S. Pat. No. 3,893,808, describes a strip of filter paper treated in bands with a chemical reagent, iodine, into which a sample of gasoline suspected of containing lead is wicked from one end and a developing reagent, dithizone, is wicked into the pretreated bands.

U.S. Pat. No. 3,895,914, describes another chemically treated test strip in which chemical reagents are applied in bands or zones on a strip for detecting barbituric acid.

U.S. Pat. No. 4,415,700, describes hydrophilic latex beads consisting of a homo- or co-polymer of monomers containing at least one epoxy group and at least one polymerizable carbon-carbon double bond in each molecule. The method using the particles is a competitive assay wherein labeled first antibody bound analyte and unlabeled first antibody bound analyte compete for binding sites on a particle bound second (anti-first antibody) antibody.

Environmental applications have been explored for the better part of a decade and a number of immunoassay methods have been developed. Most have been used for the detection of herbicides and pesticides in aqueous matrixes. The application of binding assay technology to the testing of solid waste, complex matrixes, and highly lipophilic compounds, has provided unique challenges for the chemist. The feasibility of developing such methods, however, has been demonstrated with immunoassays for single compounds such as Dioxin (see, for example, Vanderlaan, et al. Environmental Toxicology and Chemistry, 7:859–870, 1988; and Stanker, et al., Toxicology, 45: 229–243, 1987).

One of the most serious problems in environmental contamination is the presence of polychlorinated biphenyls (PCBs). PCBs, as commercially available, existed as mixtures of PCB congeners containing various mixtures of 209 different isomeric forms. Toxicological data has indicated that the highly chlorinated PCBs are the most toxic to human health. Because the composition of PCB products varies from individual product to individual product, and even from lot to lot within the same product, binding assay test development is difficult.

Testing is an essential and integral component of all environmental protection and restoration activities. It is the rate limiting element that influences the time, cost, and overall efficiency of project management.

The management of toxic waste sites usually involves a progression through the stages of identification, characterization, remediation and monitoring, with testing being performed during each phase. Reference laboratory methods can effectively identify and quantify unknown compounds in a sample, but become relatively inefficient when used to rapidly locate contamination (i.e., mapping), and assist in remediation and monitoring activities. The complexity of laboratory protocols, and the proximity of the labs to the test site, however, delays the availability of information and increases the cost of obtaining data. The ultimate cost is in the time required by the field crews to collect and test samples for the presence of contaminants. Effective field screening methods can increase the efficiency of the clean-up process by providing an on-site, high-throughput, and cost-effective way to locate contamination and manage its remediation.

The Environmental Protection Agency (EPA) has long promoted and supported the concept of screening methods to supplement laboratory analysis and increase overall efficiency. The need for more effective methods has been recognized in the Superfund Amendments and Reauthorization Act of 1986 which specifies the development and evaluation of alternative time and cost-saving methods that will assist in the eventual remediation of the nations Superfund sites.

Effective field screening methods can increase the efficiency of site management and improve overall data quality when used to supplement the services of regional laboratories. The development of these methods, however, requires a technology that will be compatible with numerous compounds and matrixes and yet be simple, effective and rugged enough to be incorporated into a protocol for use in the field.

Screening methods need to provide fast, simple, cost-effective and reliable information when operated under field conditions. The reagents and equipment should be portable and stable at ambient conditions, and the claims relating to performance should accurately reflect anticipated field use. The methods should be able to rapidly provide an ample quantity of data, and the protocol should be simple to perform and safe to use. Performance characteristics relative to sensitivity, freedom, and correlation to an acceptable reference method should be carefully evaluated. A necessary characteristic of particular significance for screening methods is that they exhibit a very low frequency of false negative results.

Screening methods detect contamination at specified concentrations. The concentration may relate to a hazardous threshold, a clean-up target, or a process-control parameter. The potential implications of false negative data far outweigh those of false positive results. The consequence of a false positive, while a costly problem that needs to be minimized, results in additional testing or treatment. False negative data, however, provides an erroneous perception of a clean site, and may have serious environmental and legal consequences. Safeguards that minimize the incidence of false negative results are imperative.

Thus, a simple binding assay method is needed which will provide reliable, accurate and fast results in the field for a wide range of PCB contaminants (regardless of manufacturer, exact composition or matrix) in a single test using a single antibody. Such an assay would increase the efficiency of environmental site management activities such as characterization (mapping), remediation monitoring, and regulatory compliance.

Similarly, the most widely used products responsible for environmental contamination are refined petroleum products. The contamination of soil and ground water by petroleum products during transport, storage, treatment and disposal is a frequent occurrence. In an attempt to establish the magnitude of the problem, a recent study by the EPA's Underground Storage Tank Program estimated that the U.S. contains approximately 1.4 million underground storage tanks and as many as 400,000 of these tanks may be leaking (see Schwenndeman, et al, in Underground Storage Systems: Leak Detection and Monitoring. Lewis Publishers, Inc., Chelsea, Mich., 1987, 16; Federal Register, Vol. 52, No. 74, 12664 (1987)).

Currently, reference methods for detecting contamination at sites include analysis for benzene, toluene, xylene, ethyl benzene and petroleum hydrocarbons. These methods require laboratory analysis by gas chromatography (GC) or infrared (IR) methods and an extended period of time to obtain the results (see Potter, in Petroleum Contaminated Soils, eds., Calabrese et al., Vol. 2, Lewis Publishers, Chelsea, Mich., 97 (1990)).

While hydrocarbon vapor analyzers can be useful because they provide rapid results, they fail to accurately reflect the amount of hydrocarbons in a soil sample and are unable to detect the more persistent contamination caused by semi-volatile components.

Thus, a binding assay method is needed which will provide reliable accurate and fast results in the field for a wide range of petroleum based contaminants, regardless of manufacturer or exact composition. Such an assay would increase the efficiency of environmental site management activities such as characterization (mapping), remediation, monitoring, and regulatory compliance.

A major disadvantage of prior art positive readout competitive binding assay devices and methods used for detecting small molecules is that the binding affinity of the analyte and its associated binding partner must be sufficiently high to prevent false positives. However, many small molecule binding pairs have insufficient affinity, thus limiting the applicability of this technology to the detection and measurement of small molecules critical for the accurate assessment of environmental quality.

There is also a great need for simple, inexpensive and easy-to-use devices that can be used in doctor offices, at clinics or at home for testing for the presence of therapeutic drugs or hormones in body fluids. Additionally, clinics, emergency medical technicians, corrections facilities, police and firemen require an affordable and easy-to-use device suitable for quickly testing for the presence of drugs of abuse in body fluids outside of a hospital setting.

Thus, a simple, inexpensive, reliable binding assay device and method that is rapid, accurate and precise, and capable of detecting and measuring small molecules and adaptable for field testing is needed.

SUMMARY OF THE INVENTION

The present invention relates to a binding device and assay method that overcome the problems of the prior art.

It is an object of the invention to provide a simple, inexpensive, reliable binding assay device and method that is rapid, accurate and precise.

It is a further object of the invention to provide a binding assay and method useful for detecting small molecules.

A feature of the invention is that the label is an indirect label, i.e. the label to be detected is not conjugated to either the analyte or to the analyte receptor, but rather is conjugated to a binding moiety capable of specifically binding to either the analyte carrier conjugate to be detected or to a diffusable analyte receptor. The labeled binding moiety-conjugate is diffusable and is provided in a limited quantity relative to the amount of label binding moiety binding partner present in the device.

Another feature of the invention is that the binding assay device provides a positive readout signal.

Another feature of the invention is that the device and method are suited for rapid and reproducible analyses.

An additional feature of the invention is that the diffusable binding partner of the binding pair of the analyte to be detected is the analyte, then the analyte is conjugated to a carrier that is capable of being bound by an immobilized binding moiety.

An advantage of the invention is that binding partners with binding affinities of less than approximately $10^{-7}$, which would not otherwise be appropriate for a positive readout competitive binding assay, can be used in a lateral flow binding device to achieve accurate and reproducible results.

Another advantage is that the binding assay device and method results in a signal that increases in proportion to the concentration of analyte in the test sample, providing an easy to visualize positive signal. In contrast, standard competitive binding assays provide a signal that is inversely related to the amount of analyte in the sample, which is difficult to assess visually.

An advantage of the limiting quantity of indirect label used in the binding assay device and method of the invention is that "bleed-through" and false positives are substantially reduced or eliminated.

Yet another advantage is that the device and method are particularly suited for field testing and screening of samples for the presence of small molecules, without the need for extensive training or expensive laboratory equipment.

The invention more specifically relates to a chromatographic strip indirect label positive readout competitive binding assay device comprising, a chromatographic strip having a length and narrow width capable of conveying fluids in a fluid flow direction generally parallel to the length of the strip, the strip comprising the following zones:

(1) a sample contact zone where fluid sample suspected of containing an analyte may be contacted with the strip;

(2) a labeled anti-first binding partner zone disposed at, or downstream from the sample contact zone comprising diffusable labeled anti-first binding partner;

(3) a first binding partner zone disposed at, or downstream from the labeled anti-first binding partner zone comprising diffusable unlabeled first binding partner in an amount sufficient to bind approximately at least all of the labeled anti-first binding partner;

(4) a trapping zone on the strip at, or downstream from the first binding partner zone comprising immobilized second binding partner in an amount sufficient to bind at least a sufficient amount of the unlabeled first binding partner to bind substantially all of the labeled anti-first binding partner; and (5) a detection zone on the strip at a downstream location from the trapping zone comprising an immobilized binding moiety specific for the first binding partner.

When the first binding partner is analyte, the first binding partner is provided as an analyte-carrier conjugate, the binding moiety desirably specifically binds the carrier portion of the conjugate, and the second binding partner is analyte receptor. When the first binding partner is analyte receptor, the second binding partner is analyte-carrier conjugate.

The device and method of the present invention permit rapid, low cost field testing and screening for important small molecules, such as environmental contaminants, drugs of abuse, therapeutic drugs and hormones.

DETAILED DESCRIPTION OF THE INVENTION

This invention permits the utilization of a low affinity binding partner for the analyte, yet avoids the problem of false positive signals common to positive readout binding assays using low affinity binding partners. The invention utilizes:

(1) a diffusable unlabeled first binding partner, which generally has low binding affinity for a second binding partner. When the first binding partner is analyte, the first binding partner is provided as analyte-carrier conjugate, wherein the carrier portion of the conjugate is capable of being bound by an immobilized binding moiety;

(2) a diffusable labeled anti-first binding partner, which usually has high binding affinity for the first binding partner;

(3) an immobilized second binding partner, which generally has low binding affinity for the first binding partner. When the second binding partner is analyte, the second binding partner is provided as analyte-carrier conjugate; and (4) an immobilized detection binding moiety capable of binding to the first binding partner.

The diffusable unlabeled first binding partner is provided in an amount sufficient to bind approximately all of the diffusable labeled anti-first binding partner, and the immobilized second binding partner is provided in an amount sufficient to bind a sufficient amount of the diffusable unlabeled first binding partner to bind approximately all of the diffusable labeled anti-binding partner.

In the absence of analyte in a sample applied to the binding device, all of the label is trapped prior to the detection zone, yielding a negative result. The presence of analyte in the sample produces a positive readout signal that increases proportionately as the amount of analyte in the sample increases.

Important terms used herein are defined as follows.

The term "analyte" refers to a chemical, toxin or compound to be measured by the device and method of the invention. The analyte is a binding partner for the analyte receptor. Generally, the analyte is a small molecule having a molecular weight of less than approximately 10,000 Daltons, desirably less than 5,000 Daltons, more desirably less than 2,000 Daltons, still more desirable less than 1,000 Daltons. The analyte may be, for example, an antigen or a ligand, or a fragment of RNA or DNA. Generally, the analyte is conjugated to another molecule, herein referred to as a carrier, thus providing a diffusable unlabeled analyte-carrier conjugate. Suitable carrier molecules include proteins, polymer particles, carbohydrate polymers, liposomes and beads.

The term "analyte receptor" refers to a molecule capable of binding specifically with the analyte. The analyte receptor may be a protein, peptide, fragment of RNA or DNA, binding moiety or otherwise a binding partner of the analyte. A novel aspect of the invention is that the positive readout binding assay device and the method of testing for analyte may employ low affinity binding partners, for example binding partners having binding constants of less than approximately $10^{-7}$, desirably approximately $10^{-5}$ to $10^{-7}$.

The analyte and the analyte receptor together are referred to as a binding pair comprising a first binding partner and a second binding partner. The analyte and the analyte receptor may be either the first binding partner or the second binding partner, respectively, depending on the particular embodiment of the invention. The analyte is generally provided in the binding device as analyte-carrier conjugate. Desirable binding pairs include antibody-antigen, antibody-hapten; and receptor-ligand binding pairs such as aryl hydrocarbon receptor—aryl hydrocarbon (e.g. dioxin, polyaromatic hydrocarbon and furan); hormone receptor—hormone (e.g. estrogen); nucleic acid hybridizing oligomers—DNA/RNA fragments (e.g. from Cryptosporidium or Giardia); artificial binding partners (e.g. molecular imprinting—the process of making molecule casts of small molecules by combining a resin with the small molecule, crosslinking or otherwise hardening the resin, grinding the resin and extracting the small molecule resulting in small molecule-specific casts capable of specifically binding the small molecule, and RNA nexamers—functionalized RNA oligomers capable of acting as a specific binding partner).

Conjugation of the analyte to form a diffusable binding partner-carrier conjugate is carried out using standard conjugation techniques well known in the art. Suitable crosslinking reagents in accordance with the present invention include, but are not limited to the following: S-acetylthioglycolic acid, N-hydroxysuccinimide ester; N-(5-azido-2-nitrobenzyloxy) succinimide; p-azidophenacyl bromide; N-(4-azidophenylthio) phthalimide; 4-azidosalicylic acid N-hydroxysuccinimide ester; bromoacetic acid N-hydroxysuccinimide ester; 1,4-butanediol diglycidyl ether; 2-diazo-3,3,3-trifluoropropionic acid p-nitrophenyl ester; dimethyl adipimidate dihydrochloride; dimethyl 3,3-dithiobispropionimidate dihydrochloride; dimethyl pimelimidate dihydrochloride; dithiobis(propionic acid N-hydroxysuccinimide ester); ethylene glycol bis-(succinic acid N-hydroxysuccinimide ester); 4-fluoro-3-nitrophenyl azide; bis(4-fluoro-3-nitrophenyl) sulfone; 4-(N-maleimido)benzophenone; g-maleimidobutyric acid N-hydroxysuccinimide ester; e-maleimidocaproic acid N-hydroxysuccinimide ester; 4-(N-maleimidomethyl) cyclohexane-1 carboxylic acid N-hydroxysuccinimide ester; β-maleimidopropionic acid N-hydroxysuccinimide ester; N,N-bis(3-maleimidopropionyl)-2 hydroxy -1,3 propanediamine; N,N-o-phenylene dimaleimide; polyoxyethylene bis (glycidyl ether); polyoxyethylene bis(imidazolyl carbonyl) and suberic acid bis(N-hydroxysuccinimide) ester, etc.

Moreover, suitable linker molecules in accordance with the present invention include, but are not limited to, the following: proteins, carbohydrates, lipids, peptides, polyesters, nucleic acids and synthetic polymers (e.g., poly-1-lysine) (See. e.g. Auotsuka, S., et al., *J. Immunol. Methods.*, 28:149–162 (1979); Presentini, R., et al.,*J. Immunol. Methods,* 10:395–412 (1989) and Vershcoor, J. A. et al., *J. Immunol. Methods,* 127:43–49 (1990), the disclosure of which are incorporated herein by reference). The linker molecule can be bifunctional (i.e., it may have two reactive sites) wherein one of the reactive sites is used for attachment to the analyte, while the other reactive site is used to attach the analyte conjugate partner. Generally, the analyte can be attached to the linker molecule and, in turn, the carrier using a cross-linking reagent, supra, in a Schiff base formation reaction with an aldehyde group; an amide formation reaction with an amine or carboxylic acid group using a peptide coupling reagent (such as, for example, carbodiimide, acid chloride and the like, supra); an ester formation reaction with a hydroxyl or carboxylic acid group using condensing agents; a sulfide formation reaction using a sulfide coupling agent, supra; an azo bond formation reaction with an aromatic diazonium salt; or other known coupling reactions for joining organic molecules. See, reviews of such methods and techniques: e.g., Kabat, E. A. *Structural Concepts In Immunology and Immunochemistry* (2nd Ed., Holt, Rinehart and Winston, N.Y. (1976); Eyzaguirre, J. *Chemical Modifications of Enzymes; Active Site Studies*(John Wiley and Sons(1982)); Wong, S. S., *Chemistry of Protein Conjugation and Cross-Linking* (CRC Press, Inc. Boca Ration, 1991); and Brinkley, M. *Bioconjugate Chem.* 3:2–13 (1992), the disclosures of which are incorporated herein by reference.

The term "label" refers to any suitable label capable of being attached or conjugated to a anti-first binding partner, and being detected and quantified. Examples of suitable labels include enzymes capable of reacting to produce a colored reaction product, such as horseradish peroxidase and alkaline phosphatase, molecules capable of producing detectable light such as bioluminescence, chemiluminescence, phosphorescence and fluorescence, and particles, such as carbon black, colored latex beads or gold particles.

The term "chromatographic strip" refers to any substrate upon which trapping zone molecules and detection zone molecules can be immobilized, and which is capable of conveying fluid in a fluid flow direction that is generally parallel to the length of the chromatographic strip. Desirable chromatographic strips comprise non-woven substrates, including without limitation nylon, polyethylene, glass fiber, and cellulose. A particularly desirable chromatographic strip is nitrocellulose. The substrate of the chromatographic strip optionally may be backed with, or laminated to, another material. Desirable backing or laminating material is polyethylene or vinyl, although other suitable materials known in the art may be used.

The term "sample contact zone" is the region, generally located at one end of the chromatographic strip, where sample is applied to the strip and from which sample fluid flows in a fluid flow direction towards the opposing, or distal, end of the strip. The sample contact zone may optionally comprise a filter material. Examples of filter material include filter paper, glass fiber, polyethylene and other suitable filter materials know to skilled artisans.

The term "binding moiety" refers to any molecule capable of specifically binding to its indicated binding partner. Generally, the binding moiety has high affinity for its binding partner, and is immobilized at the detection zone. Examples of binding moieties include polyclonal or monoclonal antibodies, or fragments of such antibodies containing the binding regions, receptors such as the dioxin receptor or hormone receptors, and fragments of RNA or DNA. Where the binding partner comprises an antibody, the binding moiety may be a second antibody, or binding portion thereof, specific for the first antibody, for example a goat anti-mouse antibody. Where the binding moiety is immobilized in the detection zone, the preferred binding partner is the diffusable unlabeled first binding partner.

The term "diffusable" refers to the ability of the molecules to flow in the fluid flow direction downstream along and throughout the chromatographic strip towards the distal end of the strip.

Having defined important terms used herein, the invention and desirable embodiments thereof will be described in detail below.

The present invention encompasses a positive readout assay device that is designed to detect important analytes, particularly small molecules such as environmental and food contaminants, chemicals, toxins and compounds, metabolites such as hormones, drugs of abuse, and therapeutic drugs and metabolic byproducts thereof. These analytes are generally small molecules, which in the past have been difficult to detect and measure accurately and reproducibly in the field by non-technical personnel using binding assays.

By positive readout is meant a competitive binding assay providing a signal that increases proportionally as the concentration of analyte in the test sample increases. The positive readout feature of the invention provides an easy to determine indication of a positive result. This is a substantial improvement over standard lateral flow competitive binding assays.

Typically small molecules are detected and quantified using a standard competitive inhibition assay which results in an inverse relationship between analyte concentration and signal generation. As the concentration of the analyte in a test sample increases, the signal generated from the assay decreases. Thus, in standard competitive binding assays the greatest signal generation occurs when the analyte is absent from the test sample. Therefore, it is difficult to visually determine a low concentration of analyte because the signal change is from a dark color to a slightly less dark color.

An improvement of the competitive assay format provided by the present invention is the development of a positive readout assay, e.g., an assay in which the signal increases a person's ability to visually detect low concentrations of analyte. The detection of a lightly colored band on a white membrane is much easier to see than a slight decrease in a dark band on the membrane.

The invention also encompasses a method of testing for analytes using the binding assay device. A novel aspect of the invention is the ability to use binding pairs having binding affinities of less than $10^{-7}$, desirably between $10^{-5}$ and $10^{-7}$.

Figure 1:
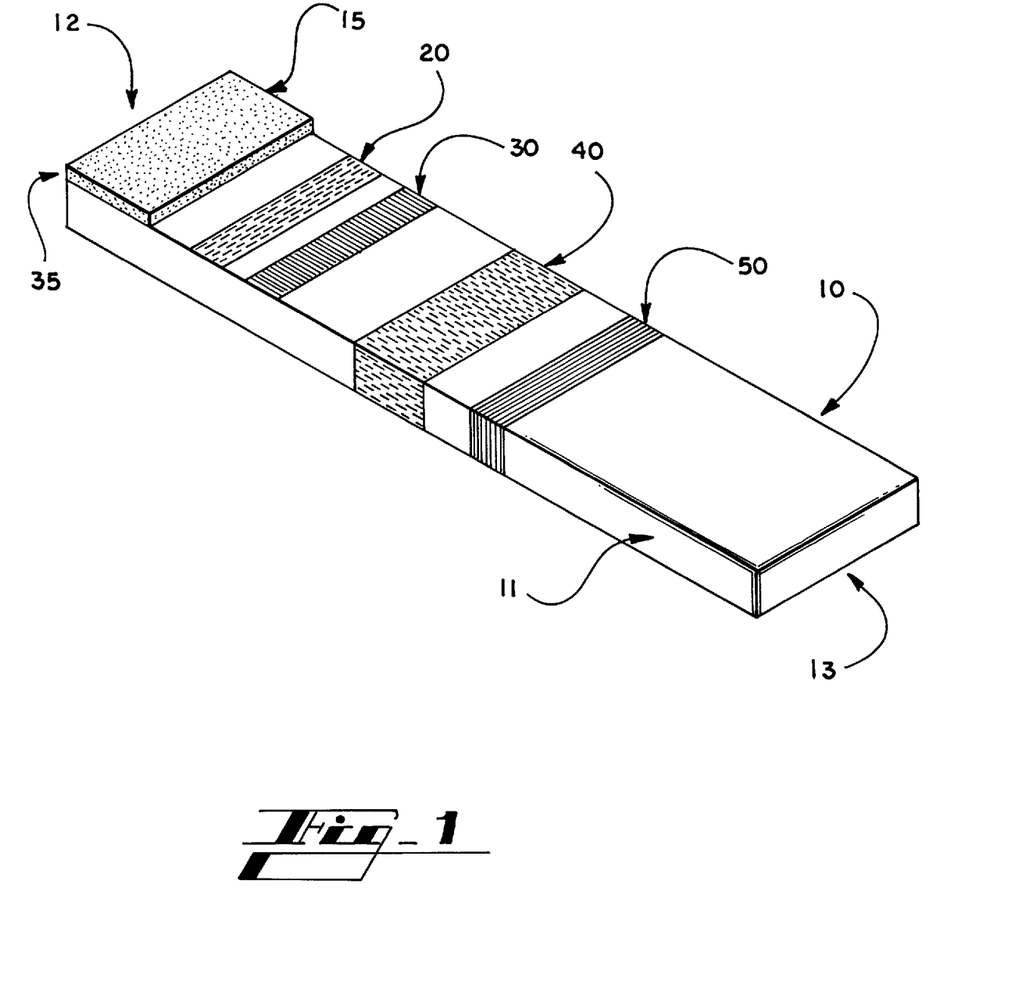
FIG. 1 is a schematic drawing of a binding assay device.

Referring to FIG. 1, the binding assay device of the invention comprises, a chromatographic strip 10, comprised of a substrate 11, generally having a length and narrow width with a proximal end 12 and a distal end 13, which is capable of conveying fluids in a fluid flow direction generally parallel to the length of the strip. The chromatographic strip comprises multiple zones. A sample contact zone 15 located at the proximal end of the strip, is the region where fluid sample suspected of containing an analyte may be contacted with the strip. A diffusable labeled anti-first binding partner zone 20, is disposed downstream (towards the distal end of the strip) from the sample contact zone 15 comprising diffusable labeled binding moiety capable of binding a first binding partner. The first binding partner is either analyte or analyte receptor. When the first binding partner is analyte, the first binding partner is desirably a conjugate of analyte and carrier. The labeled anti-first binding partner may specifically bind any portion of the first binding partner, including the carrier portion when it is a conjugate. An unlabeled first binding partner zone 30 is disposed downstream from the anti-first binding partner zone 20. The unlabeled first binding partner is provided in an amount sufficient to bind approximately all of the diffusable labeled anti-first binding partner. A trapping zone 40 is immobilized on the strip at a downstream location from zones 20 and 30, comprising second binding partner in an amount sufficient to bind at least a sufficient amount of the diffusable first binding partner to bind substantially all of the diffusable labeled anti-first binding partner. Finally, a detection zone 50 is immobilized on the strip at a downstream location from trapping zone 40 comprising a binding moiety specific for the first binding partner, desirably the carrier when the first binding partner is a conjugate. The anti-first binding partner of zone 20 may optionally be the same as the binding moiety of zone 50.

For clarity each zone is depicted as being separated from every other zone. However, one or more zones may be coincident or overlap, with the exception of the detection zone, which must always be separate and downstream from the other zones.

In another embodiment of the invention, the labeled anti-first binding partner zone, or first binding partner zone, or both, are not placed on the strip. In these embodiments, the labeled anti-first binding partner, or first binding partner, or both, are combined with the sample prior to application of the sample to the sample contact zone. The thus formed mixture of sample and assay components is then applied to the sample contact zone.

One embodiment of the method entails combining both diffusable assay components with the sample prior to applying the sample-assay component mixture to the binding assay device. More particularly, the presence and amount of an analyte in a sample suspected of containing the analyte is detected by employing a chromatographic strip-positive readout binding assay device, the binding assay device comprising, a chromatographic strip having a length and narrow width capable of conveying fluids in a fluid flow direction generally parallel to the length of the strip, the strip comprising;

a sample contact zone whereat fluid sample suspected of containing an analyte may be contacted with the strip;

a trapping zone located at, or downstream from, the sample contact zone comprising immobilized second binding partner in an amount sufficient to bind at least a sufficient amount of the unlabeled first binding partner to bind substantially all of the labeled anti-first binding partner; and a detection zone located on the strip downstream from the trapping zone comprising an immobilized binding moiety specific for the diffusable unlabeled first binding partner, wherein the sample to be tested is combined with diffusable labeled anti-first binding partner and diffusable unlabeled first binding partner to form a sample-assay component mixture, and the sample-assay component mixture is applied to the sample contact zone, and the presence of label in the detection zone is detected.

Another embodiment employs a chromatographic strip-positive readout binding assay device, the binding assay device comprising, a chromatographic strip having a length and narrow width capable of conveying fluids in a fluid flow direction generally parallel to the length of the strip, the strip comprising;

a sample contact zone whereat fluid sample suspected of containing an analyte may be contacted with the strip;

a labeled anti-first binding partner zone disposed at, or downstream from the sample contact zone comprising diffusable labeled anti-first binding partner;

a trapping zone located at, or downstream from, the sample contact zone comprising immobilized second binding partner in an amount sufficient to bind at least a sufficient amount of the unlabeled first binding partner to bind substantially all of the labeled anti-first binding partner; and a detection zone located on the strip downstream from the trapping zone comprising an immobilized binding moiety specific for the diffusable unlabeled first binding partner, wherein a sample to be tested is combined with diffusable unlabeled first binding partner to form a sample-assay component mixture, the sample-assay component mixture is applied to the sample contact zone, and the presence of label in the detection zone is detected.

Yet another embodiment employs a chromatographic strip-positive readout binding assay device, the binding assay device comprising, a chromatographic strip having a length and narrow width capable of conveying fluids in a fluid flow direction generally parallel to the length of the strip, the strip comprising;

a sample contact zone whereat fluid sample suspected of containing an analyte may be contacted with the strip;

a first binding partner zone disposed at, or downstream from the sample contact zone comprising diffusable unlabeled first binding partner in an amount sufficient to bind approximately all of a labeled anti-first binding partner in a sample-assay component mixture to be applied to the binding device;

a trapping zone located at, or downstream from, the sample contact zone comprising immobilized second binding partner in an amount sufficient to bind at least a sufficient amount of the unlabeled first binding partner to bind substantially all of the labeled anti-first binding partner; and a detection zone located on the strip downstream from the trapping zone comprising an immobilized binding moiety specific for the diffusable unlabeled first binding partner, wherein a sample to be tested is combined with diffusable labeled anti-first binding partner to form a sample-assay component mixture, the sample-assay component mixture is applied to the sample contact zone, and the presence of label in the detection zone is detected.

The sample contact zone 15 may optionally comprise a filter material overlay 35 through which the sample flows to reach the sample contact zone. Additionally, absorbent material may be attached to the distal end of the chromatographic strip to facilitate the flow of sample fluid from the sample contact zone past the downstream zones. A cover or casing having openings for the sample contact zone and the detection zone may overlay or surround the chromatographic strip. The cover or casing desirably is made of non-absorbent material such as plastic.

The cover or casing optionally may be formed so as to provide a volumetric container into which the sample is introduced. The container may be either integral with the cover or casing, or be separate from the cover or casing, but attachable to the cover or casing at the sample contact zone opening so as to form a volumetric cavity into which sample is introduced. The sample may be poured or otherwise introduced into the volumetric container to a predetermined volume, for example to the top of the container, or to a line scribed, printed or embossed on the side of container. Alternatively, the container may contain an opening such as a slot or hole such that when the container is submerged in sample and withdrawn, excess sample volume runs out of the container.

It is believed that because there is an excess unlabeled first binding partner and of immobilized second binding partner, relative to the concentration of labeled anti-first binding partner present in the device, the labeled anti-first binding partner is essentially completely bound by the first binding partner which, itself, is bound to the immobilized second binding partner, thereby preventing bleed-through and false positives. Even low affinity binding partners, having a binding affinity of less than approximately $10^{-7}$ may be used in the binding assay of the invention.

The method of the invention comprises applying sample to be tested, or a mixture of sample and assay components as described above, to the sample contact zone and detecting the presence, and optionally the amount, of label captured at the detection zone. The application of sample may be by any standard application, for example via dropper, syringe, pipet or pouring, or by dipping the chromatographic strip in sample such that sample contacts the sample contact zone.

The detection of the label may be any standard visualization, detection or measurement means known in the art. Desirable methods for detecting and quantifying the label in the binding assay invention include enzymatic color generation, radioactive detection such as by X-ray exposure of films or scintillation or gamma counting, depending on the isotope utilized, luminescent measurements where the label produces bioluminescent or chemiluminescent light, and fluorescent. Desirable detection methods are visual assessment, color change, for example due to pH shift, and measurement amount of colored label with a hand-held reflectometer.

Prior to application of sample to the binding assay device, the sample may be pre-treated to extract, concentrate or release the analyte to be detected. For example soil samples may be methanol treated to extract contaminants, toxins or compounds whose presence and quantity are useful as indicia of the environmental quality of the soil being tests.

Multiple analytes may be tested simultaneously according to the present invention. For example, multiple diffusable labeled binding partners for various analyte binding pairs could be applied to a binding assay device. The presence of label at the detection zone indicates that at least one of the analytes for which the device is sensitive is present in the sample. In this way rapid screening of multiple environmental factors can be conducted with a minimum number of test, at a reduced cost, and in an expedient fashion.

Alternatively, the binding assay device of the invention may incorporate multiple diffusable label binding partners as described above in combination with multiple detection zones, each zone being specific for an individual analyte-specific label. This device provides a means for rapid, low cost environmental screening, while retaining the ability to discriminate between, and quantify, various specific analytes.

In one embodiment the diffusable labeled anti-first binding partner is labeled anti-BSA antibody, the diffusable unlabeled first binding partner-carrier conjugate is PCB-BSA, the immobilized second binding partner is anti-PCB antibody, and the detection binding moiety is anti-BSA antibody.

In another embodiment the diffusable labeled anti-first binding partner is labeled goat anti-mouse antibody, the diffusable unlabeled first binding partner-carrier conjugate is anti-PCB antibody, the immobilized second binding partner is PCB-BSA, and the detection binding moiety is anti-mouse antibody.

The invention may be further understood by reference to the following non-limiting detailed examples.

Example 1—Analyte diffusable and analyte receptor immobilized.

I. Membrane Coating

A. Cut membranes in 0.8 cm×5 cm strips

B. Dilute goat anti-mouse IgG to 1 mg/ml in phosphate buffered saline (PBS)
C. Add goat anti-mouse about 2.0 cm from top of strip
D. Add anti-fluorescein (1 mg/mL) about 1.0 cm from top of strip
E. Dry strips
F. Block strips with PBS/Casein (0.5%) for 30 minutes
G. Dry strips
H. Anti-PCB antibody (approx. 100 mg/mn) in PBS is applied to the goat anti-mouse IgG band
I. The strip is dried, washed and dried again
J. Add PCB-BSA-FITC (10 mg/mL) 2.5 cm from top
K. Add Anti-fluorescein gold particles in Tris/BSA buffer (Tris (20 mM), BSA (1%), sodium azide (0.1%), pH 8.2) containing 30% sucrose about 3 cm from top of the strip
L. Dry strip II. Protocol for Coating Gold Particles with Rabbit anti-fluorescein IgG
A. Adjust pH of gold to about 9. Add final concentration of 5 mM sodium borate ($Na_2B_4O_7$), pH=9.2
B. Dialyze rabbit anti-fluorescein against 2 mM borate (pH 9.2). 3 changes of 100×column of antibody for 24 hour. Antibody should be >2 mg/mL.
C. Add 0.06 mg Ab/mL of gold—rapidly mix
D. Incubate for 2–15 min. at RT
*Check spectrum between 450–800 nm
*Compare gold solution (50 mL) diluted into water (450 mL) and into 10% NaCl solution (450 mL)
*If spectrum do not match, then the gold particles have not absorbed enough protein and one should add another 0.03 mg Ab/mL gold. Continue adding antibody until spectrum match. The spectrum for the salt containing sample will be slightly lower than the water sample but it should have the same shape.
E. Add 1/10 volume 10% BSA in water=final of 1% BSA. Mix rapidly upon addition and incubate 2–15 minutes at RT.
F. Centrifuge for 5 min @ 10,000× g. Discard supernatant.
G. Resuspend pellet in Tris (20 mM), BSA (1%), sodium azide (0.1%), pH 8.2, using ½ the original volume.
H. Centrifuge for 5 min @ 8,000× g. Discard supernatant. Resuspend pellet in Tris/BSA buffer.
I. Repeat washes two more time. The last spin may require 10,000× g.
J. Resuspend pellet in ⅕ original volume III. Preparation of PCB-BSA-FITC
A. Dissolve BSA (Fraction V) in Potassium Phosphate (0.2M, pH 8) at 10 mg/mL.
B. Use PCB activated with the n-hydroxysuccinimidyl ester (PCB-NHS) at 54 mmoles/mL.
C. Make BSA solution 33% DMF include volume of PCB-NHS (total of 0.5 mL per mL BSA)
*Add 446 mL DMF per 10 mg BSA, mix
*Vortex while adding 54.4 mL of PCB-NHS per 10 mg BSA (20 fold excess)
D. Incubate 1 hour at RT
E. Centrifuge for 5 min. at 14,000 rpm
F. Put the supernatant through a G-25 column (1.5 mL for each disposable 10 mL column ) equilibrated with PBS/0.05% azide.
G. Collect protein fraction
H. Dissolve FITC in DMF and add a 20 fold molar excess to the PCB-BSA conjugate. Incubate for 1 hour at room temperature.
I. Purify using a G-25 column as in step F.
J. Collect protein fraction IV. Assay
A. Attach an absorbent pad to top and bottom end of strip.
B. Add several drops of sample to bottom absorbent pad of the strip and allow to "wick" up the strip.
C. Allow sample to wick up entire length of strip.
D. If color develops in the detection zone (approx. 1 cm from end of strip), then the sample contains PCB.

Example 2

The binding device of Example 1, except that PCB-HRP conjugate is substituted for the PCB-BSA conjugate. The PCB-HRP conjugate is made as follows.
A. Dissolve 16 mg of HRP in 1 mL of distilled water
B. Add 2 mg of $NaIO_4$, incubate for 10 min at RT.
C. Purify the HRP on a G-25 column equilibrated with 200 mM sodium carbonate buffer at pH 9.
D. Add 1 mg of PCB-hydrazide at 10 mg/mL in methanol.
E. Incubate for 1 hour at room temperature.
F. Add 1.5 mg of $NaBH_4$, incubate for 50 min at 4° C.
G. Dialyze against 3 changes of phosphate buffered saline buffer overnight.

Example 3—Analyte receptor diffusable, analyte immobilized.

I. Membrane Coating:
A. Cut membranes in 0.8 cm×5 cm strips
B. Dilute goat anti-mouse IgG to 5 mg/ml in phosphate buffered saline (PBS)
C. Add goat anti-mouse about 1.0 cm from top of strip
D. Add PCB-BSA analyte-conjugate (10 mg/mL) about 2.0 cm from top of strip
E. Dry strips at 37° C. for 15 minutes
F. Block strips with PBS/Casein (0.5%) for 30 minutes
G. Dry strips at 37° C. for 1 hour
H. Add anti-PCB antibody (approx. 10 mg/mL) in PBS and 30% sucrose about 2.5 cm from top of strip
I. Add goat anti-mouse gold particles in Tris/BSA buffer (Tris (20 mM), BSA (1%), sodium azide (0.1%), pH 8.2) containing 30% sucrose about 3 cm from the top of the strip
J. Dry strip at 37° C. for 1 hour
K. Perform assay (see Section IV)

II. Protocol for Coating gold particles with goat anti-mouse IgG
A. Adjust pH of gold particle suspension to about 9. Add final concentration of 5 mM sodium borate ($Na_2B_4O_7$), pH=9.2
B. Dialyze goat anti-mouse IgG against 2 mM borate (pH 9.2). 3 changes of 100×volume of antibody for 24 hours. Antibody concentration should be>2 mg/mL
C. Add 0.06 mg Ab/mL of gold—rapidly mix
D. Incubate for 2–15 minutes at room temperature
* Check spectrum between 450–800 nm
* Compare gold solution (50 mL) diluted into water (450 mL) and into 10% NaCl solution (450 mL).
* If spectrum do not match, then the gold particles have not absorbed enough protein and one should add another 0.03 mg Ab/mL gold. Continue adding antibody until spectrum match.
E. Add 1/10 volume 10% BSA in water=final of 1% BSA. Mix rapidly upon addition and incubate 2–15 minutes at room temperature.
F. Centrifuge for 5 minutes at 10,000× g. Discard supernatant.
G. Resuspend pellet in Tris (20 mM), BSA (1%), sodium azide (0.1%), pH 8.2, using ½ the original volume. Vortexing should be sufficient to completely resuspend pellet.
H. Centrifuge for 5 minutes at 8,000× g. Discard supernatant. Resuspend pellet in Tris/BSA buffer.

I. Repeat wash two more times. The last spin may require 10,000× g

J. After last spin, resuspend pellet in ⅕ original volume

III. Preparation of PCB-BSA

A. Dissolve BSA (Fraction V) in Potassium Phosphate (0.2M, pH 8) at 10 mg/mL

B. Use PCB activated with the n-hydroxysuccinimidyl ester (PCB-NHS) at 54 mmoles/mL C. Make BSA solution 33% DMF

* Add 446 mL DMF per 10 mg BSA, mix Vortex while adding 54.4 mL of PCB-NHS per 10 mg BSA (20 fold excess)

D. Incubate 1 hour at room temperature

E. Centrifuge for 5 minutes at 14,000 rpm

F. Put the supernatant through a G-25 column (1.5 mL for each disposable 10 mL column), equilibrated with PBS/0.05% azide.

G. Collect protein fraction

IV. Assay

A. Attach an absorbent pad to top and bottom end of strip

B. Add several drops of sample to bottom absorbent pad of the strip and allow to "wick" up the strip C. Allow sample to wick up entire length of strip D. If color develops in the detection zone (approximately 1 cm from end of strip), then the sample contains PCB.

While the invention has been described in connection with a preferred embodiment, it is not intended to limit the scope of the invention to the particular form set forth, but, on the contrary, it is intended to cover such alternatives, modifications and equivalents as may be included within the spirit and scope of the invention as defined by the appended claims.

I claim:

1. A chromatographic strip positive readout competitive binding assay device comprising, a chromatographic strip with a proximal end and a distal end having a length and narrow width that conveys fluids in a fluid flow direction along the length toward the distal end of the strip, the strip comprising the following zones;

a sample contact zone where fluid sample suspected of containing an analyte may be contacted with the strip;

a labeled anti-first binding partner zone disposed at, or downstream from the sample contact zone comprising diffusable labeled anti-first binding partner;

a first binding partner zone disposed at, or downstream from the labeled anti-first binding partner zone comprising diffusable unlabeled first binding partner that binds to the labeled anti-first binding partner to form a diffusable first binding partner/anti-first binding partner complex, wherein the first binding partner of the first binding partner/anti-first binding partner complex is analyte receptor that binds to analyte in the sample;

a trapping zone on the strip at, or downstream from the first binding partner zone comprising immobilized second binding partner that binds to the first binding partner/anti-first binding partner complex that is not bound to analyte in the sample; and a detection zone located on the strip downstream from the trapping zone comprising an immobilized binding moiety specific for the diffusable first binding partner/anti-first binding partner complex that is not bound to the immobilized second binding partner, wherein the detection of label in the detection zone indicates the presence of analyte in the sample.

2. The binding device of claim 1, wherein the immobilized second binding partner is analyte-carrier conjugate.

3. The binding assay device of claim 1, wherein the first binding partner is selected from the group consisting of antibodies, aryl hydrocarbon receptors, hormone receptors, nucleic acid hybridizing oligomers, and synthetic binding partners, and the second binding partner is selected from the group consisting of antigens, haptens, aryl hydrocarbons, hormones, and DNA/RNA fragments.

4. The binding assay device of claim 1, wherein the label is selected from the group consisting of colored latex beads, gold particles, carbon black, horseradish peroxidase, alkaline phosphatase, bioluminescent photoproteins, and chemiluminescent compounds.

5. The binding assay device of claim 1, further comprising filter material overlaid on the sample contact zone.

6. The binding assay device of claim 1, further comprising absorbent material attached to the distal end of the chromatographic strip.

7. A method for detecting the presence and amount of an analyte in a sample suspected of containing the analyte, the method employing a chromatographic strip-positive readout binding assay device, the binding assay device comprising, a chromatographic strip with a proximal end and a distal end having a length and narrow width that conveys fluids in a fluid flow direction along the length toward the distal end of the strip, the strip comprising the following zones;

a sample contact zone where fluid sample suspected of containing an analyte may be contacted with the strip;

a labeled anti-first binding partner zone disposed at, or downstream from the sample contact zone comprising diffusable labeled anti-first binding partner;

a first binding partner zone disposed at, or downstream from the labeled anti-first binding partner zone comprising diffusable unlabeled first binding partner that binds to the labeled anti-first binding partner to form a diffusable first binding partner/anti-first binding partner complex, wherein the first binding partner of the first binding partner/anti-first binding partner complex is an analyte receptor that binds to analyte in the sample;

a trapping zone on the strip at, or downstream from the first binding partner zone comprising immobilized second binding partner that binds to the first binding partner/anti-first binding partner complex that is not bound to analyte in the sample; and a detection zone located on the strip downstream from the trapping zone comprising an immobilized binding moiety specific for the diffusable first binding partner/anti-first binding partner complex that is not bound to the immobilized second binding partner, the method comprising, adding the sample to the sample contact zone and detecting the presence of label in the detection zone, wherein the detection of label in the detection zone indicates the presence of analyte in the sample.

8. The method of claim 7, wherein the immobilized second binding partner is analyte-carrier conjugate.

9. The method of claim 7, wherein the first binding partner is selected from the group consisting of antibodies, aryl hydrocarbon receptors, hormone receptors, nucleic acid hybridizing oligomers, and synthetic binding partners, and the second binding partner is selected from the group consisting of antigens, haptens, aryl hydrocarbons, hormones, and DNA/RNA fragments.

10. The method of claim 7, further comprising filter material overlaid on the sample contact zone.

11. The method of claim 7, further comprising absorbent material attached to the distal end of the chromatographic strip.

12. The method of claim 9, further comprising pretreating the sample prior to applying the sample to the sample contact zone, wherein the pretreatment extracts, concentrates or releases analyte from the sample.

13. The method of claim 7, wherein the label is selected from the group consisting of colored latex beads, gold particles, carbon black, horseradish peroxidase, alkaline phosphatase, bioluminescent photoproteins, and chemiluminescent compounds.

14. The method of claim 13, further comprising measuring the amount of color localized at the detection zone.

15. A chromatographic strip positive readout competitive binding assay device comprising, a chromatographic strip with a proximal end and a distal end having a length and narrow width that conveys fluids in a fluid flow direction along the length toward the distal end of the strip, the strip comprising the following zones;

a sample contact zone where fluid sample suspected of containing an analyte may be contacted with the strip;

a labeled anti-first binding partner zone disposed at, or downstream from the sample contact zone comprising diffusable labeled anti-first binding partner;

a first binding partner zone disposed at, or downstream from the labeled anti-first binding partner zone comprising diffusable unlabeled first binding partner that binds to the labeled anti-first binding partner to form a diffusable first binding partner/anti-first binding partner complex, wherein the first binding partner of the diffusable first binding partner/anti-first binding partner complex is a conjugate of analyte and carrier;

a trapping zone on the strip at, or downstream from the first binding partner zone comprising immobilized second binding partner that binds to analyte, wherein the analyte of the unlabeled first binding partner-labeled anti-first binding partner complex binds to immobilized second binding partner that is not bound to analyte in the sample; and a detection zone located on the strip downstream from the trapping zone comprising an immobilized binding moiety specific for the diffusable first binding partner/anti-first binding partner complex that is not bound to the immobilized second binding partner, wherein the detection of label in the detection zone indicates the presence of analyte in the sample.

16. The binding device of claim 15, wherein the immobilized second binding partner is analyte receptor.

17. The binding assay device of claim 15, wherein the second binding partner is selected from the group consisting of antibodies, aryl hydrocarbon receptors, hormone receptors, nucleic acid hybridizing oligomers, and synthetic binding partners, and the first binding partner is selected from the group consisting of antigens, haptens, aryl hydrocarbons, hormones, and DNA/RNA fragments.

18. The binding assay device of claim 15, wherein the label is selected from the group consisting of colored latex beads, gold particles, carbon black, horseradish peroxidase, alkaline phosphatase, bioluminescent photoproteins, and chemiluminescent compounds.

19. The binding assay device of claim 15, further comprising filter material overlaid on the sample contact zone.

20. The binding assay device of claim 15, further comprising absorbent material attached to the distal end of the chromatographic strip.

21. A method for detecting the presence and amount of an analyte in a sample suspected of containing the analyte, the method employing a chromatographic strip-positive readout binding assay device, the binding assay device comprising, a chromatographic strip with a proximal end and a distal end having a length and narrow width that conveys fluids in a fluid flow direction along the length toward the distal end of the strip, the strip comprising the following zones;

a sample contact zone where fluid sample suspected of containing an analyte may be contacted with the strip;

a labeled anti-first binding partner zone disposed at, or downstream from the sample contact zone comprising diffusable labeled anti-first binding partner;

a first binding partner zone disposed at, or downstream from the labeled anti-first binding partner zone comprising diffusable unlabeled first binding partner that binds to the labeled anti-first binding partner to form a diffusable first binding partner/anti-first binding partner complex, wherein the first binding partner of the first binding partner/anti-first binding partner complex is a conjugate of analyte and carrier;

a trapping zone on the strip at, or downstream from the first binding partner zone comprising immobilized second binding partner that binds to analyte, wherein the analyte of the unlabeled first binding partner-labeled anti-first binding partner complex binds to immobilized second binding partner that is not bound to analyte in the sample; and a detection zone located on the strip downstream from the trapping zone comprising an immobilized binding moiety specific for the diffusable first binding partner/anti-first binding partner complex that is not bound to the immobilized second binding partner, the method comprising, adding the sample to the sample contact zone and detecting the presence of label in the detection zone, wherein the detection of label in the detection zone indicates the presence of analyte in the sample.

22. The method of claim 21, wherein the immobilized second binding partner is analyte receptor.

23. The method of claim 21, wherein the second binding partner is selected from the group consisting of antibodies, aryl hydrocarbon receptors, hormone receptors, nucleic acid hybridizing oligomers, and synthetic binding partners, and the first binding partner is selected from the group consisting of antigens, haptens, aryl hydrocarbons, hormones, and DNA/RNA fragments.

24. The method of claim 21, further comprising filter material overlaid on the sample contact zone.

25. The method of claim 21, further comprising absorbent material attached to the distal end of the chromatographic strip.

26. The method of claim 21, further comprising pretreating the sample prior to applying the sample to the sample contact zone, wherein the pretreatment extracts, concentrates or releases analyte from the sample.

27. The method of claim 21, wherein the label is selected from the group consisting of colored latex beads, gold particles, carbon black, horseradish peroxidase, alkaline phosphatase, bioluminescent photoproteins, and chemiluminescent compounds.

28. The method of claim 27, further comprising measuring the amount of color localized at the detection zone.

* * * * *

UNITED STATES PATENT AND TRADEMARK OFFICE
CERTIFICATE OF CORRECTION

PATENT NO. : 5,874,216

DATED : February 23, 1999

INVENTOR(S) : James P. Mapes

It is certified that error appears in the above-identified patent and that said Letters Patent is hereby corrected as shown below:

On the title page, item [73]
Assignee: Strategic Diagnostics, Inc.

Signed and Sealed this

Second Day of May, 2000

Attest:

Q. TODD DICKINSON

*Attesting Officer*     *Director of Patents and Trademarks*